United States Patent [19]

Chow et al.

[11] Patent Number: 4,859,462

[45] Date of Patent: Aug. 22, 1989

[54] POLYMER-TREATED ION EXCHANGE RESINS

[75] Inventors: San-Laung Chow; Yegnaswami Raghunathan, both of Perinton, N.Y.

[73] Assignee: Fisons Corporation, Rochester, N.Y.

[21] Appl. No.: 46,379

[22] Filed: May 4, 1987

Related U.S. Application Data

[63] Continuation of Ser. No. 892,168, Jul. 30, 1986, abandoned.

[51] Int. Cl.⁴ .................. A61K 3/74; A61K 3/78; A61K 3/79
[52] U.S. Cl. ....................... 424/79; 424/80; 424/81; 424/496
[58] Field of Search ............ 424/19, 79, 80, 81

[56] References Cited

U.S. PATENT DOCUMENTS 3,947,572  3/1976  Borodkin ................ 424/79
4,221,778  9/1980  Raghunathan ............ 424/79

FOREIGN PATENT DOCUMENTS 171528  2/1986  European Pat. Off. ........ 424/79
982150  2/1965  United Kingdom .......... 424/79

OTHER PUBLICATIONS

*Remington's Pharmaceutical Sciences*, pp. 1244–1247 and 1260 (1980) (16th ed.).
*Remington's Pharmaceutical Sciences*, 15th ed. pp. 1254–1255, (1975).

*Primary Examiner*—Dale R. Ore
*Attorney, Agent, or Firm*—Seidel, Gonda, Lavorgna & Monaco

[57] ABSTRACT

Sulfonic acid cationic exchange resin particles which have been treated to improve their coatability with minor amounts of high molecular weight polymers selected from carboxypolymethylene, xanthan gum, and propylene glycol alginate.

4 Claims, No Drawings

POLYMER-TREATED ION EXCHANGE RESINS

This application is a continuation of application Ser. No. 892,168, filed July 30, 1986, now abandoned.

The present invention relates to sulfonic acid cationic exchange resin particles which have been treated with a minor amount of a high molecular weight polymer to improve the particles coatability, to methods for treating the particles with such polymers and to selective, prolonged continuous release pharmaceutical preparations made therefrom. As described in U.S. Pat. No. 4,221,778, the contents of which are incorporated herein by reference, such preparations contain ion exchange resin particles having a pharmacologically active drug adsorbed thereon to form drug-resin complex particles, at least a portion of which particles are treated with an impregnating agent and provided with a diffusion barrier coating.

BACKGROUND

U.S. Pat. No. 4,221,778 discloses that controlled (i.e., selective, prolonged) continuous release of pharmacologically active drugs, under conditions such as those encountered in the gastrointestinal tract, can be achieved by the application of diffusion barrier coatings to ion exchange resin drug complex particles which have been treated, prior to coating, with an impregnating agent selected from polyethylene glycol, propylene glycol, manitol, lactose, and methylcellulose.

BRIEF SUMMARY OF THE INVENTION

The present invention is concerned (a) with sulfonic acid cationic exchange resin particles which have been treated to improve their coatability with up to about 1.1 percent by weight (based on the combined weight of the particles and the polymeric treating agent) of an effective amount of a high molecular weight polymer selected from carboxypolymethylene, xanthan gum, and propylene glycol alginate, (b) with such resin particles which have a basic drug adsorbed thereon to form drug-resin complex particles, (c) with such drug-resin complex particles which have been coated, subsequent to treatment with the polymer, with a water-permeable diffusion barrier, and (d) with pharmaceutical preparations comprised of such coated drug-resin complex particles, as well as with the method for enhancing the coatability of the resin particles by contacting them with an aqueous solution containing up to about 1.1% by weight of the high molecular weight polymer, based on the combined weight of the polymer and the particles. Prolonged continuous release of the drug is obtainable from such preparations under conditions encountered in the gastrointestinal tract.

By varying the amount of coating, and/or by blending coated drug-resin complex particles with uncoated drug-resin complex particles, it is possible to selectively modify the preparation's drug dissolution profile as desired.

The ion exchange resins, drugs, and coatings, and methods for preparing drug-resin complexes, for coating of the complexes, and for selectively modifying the preparation's dissolution profile through blending and/or degree of coating, are disclosed and exemplified in U.S. Pat. No. 4,221,778, said disclosure and examples being herein incorporated by reference.

DETAILED DESCRIPTION

While U.S. Pat. 4,221,778 disclosed that about 10 to 25% by weight of a treating agent was normally needed to improve the resin's coatability, it has now been found that the aforementioned polymeric treating agents of this invention need only be used in amounts of from at least about 0.04 percent up to about 1.1 percent by weight, based on the weight of the resin and the polymer (equivalent to about 0.03 to 0.8 percent by weight based on the weight of the drug-resin complex and the polymer). The carboxypolymethylene (such as Carbopol ® 934P, described by the manufacturer as a high purity grade acrylic acid polymer having a molecular weight of approximately 3,000,000) is normally used at a level of from about 0.1 to about 1.1% by weight (preferably 0.4 to 0.8%); the xanthan gum is normally used at a level of from about 0.04 to about 0.20% by weight (preferably 0.07 to 0.16%); and the propylene glycol alginate is normally used at a level of from about 0.3 to about 0.9% by weight (preferably 0.5 to 0.7%); all such percentages being based on the combined weight of the resin and the polymer. The resin particles are preferably treated by contacting them with an aqueous solution of the polymer. As shown in Table I hereinafter, treatment of the resin with the polymers of this invention (Examples 1 to 3), in comparison to untreated resin (Comparative Example), enhanced the resin's coatability as evidenced by the significantly greater retardation in the drug release rate in the coated drug-resin complexes made from the treated resin.

In general, all pharmacologically active basic drugs, especially those having short biological half-lives in the order of up to about eight hours, are potential candidates for inclusion in the subject preparations. Examples include, but are not limited to, phenylpropanolamine (PPA), dextromethorphan, codeine, hydrocodone, hydralazine, propranolol, doxepin, metaproterenol, morphine, ephedrine, pseudophedrine, and verapamil. PPA, a sympathomimetic amine drug with a biological half life of 3.9 hours in man and a pKa of 9.4, was chosen as a model drug for use in the illustrative examples. The loading of the drug on the resin particles can be from about 1 to about 90 percent by weight, although 15 to 50 percent is the normal practical range.

The resin is a sulfonic acid cationic exchange resin, normally in particle sizes ranging from about 25 to about 1000 $\mu$m. The illustrative examples employ Amberlite ® IRP-70 resin, a cationic exchange resin which is 100–200 mesh (75–150 $\mu$m) fractured resin particles of Amberlite IR-120. The parent resin of Amberlite IR-120 and Amberlite IRP-70 is described by the manufacturer as a gel-type divinylbenzene sulfonic acid cationic exchange resin which swells in water with a pH range of 0–14. The resin should not have inherent pharmacological or toxic properties.

Adsorption of the drug onto the ion exchange resin particles to form the drug resin complex is a well known technique as shown in U.S. Pat. Nos. 2,990,332 and 4,221,778. In general the drug is mixed with an aqueous suspension of the resin, and the complex is then washed and dried. Adsorption of drug onto the resin may be detected by a change in the pH of the reaction medium.

The water-permeable, diffusion barrier coating material can in general be any of the conventional synthetic or natural film-forming materials with diffusion barrier properties and with no inherent pharmacological or toxic properties. Ethylcellulose (U.S.P. grade), a water insoluble film-forming agent was used as the model diffusion barrier membrane material in the illustrative examples. A plasticizer, Durkex® 500 vegetable oil, was used to improve the film-forming characteristics of ethylcellulose. The amount of ethylcellulose film coating used depends on the degree of drug release prolongation desired.

Conventional coating solvents (such as ethanol, or a methylene chloride/acetone mixture, or coating emulsions) and coating procedures (such as fluid bed coating) can be employed to coat the particles. Techniques of fluid bed coating are taught, for example, in U.S. Pat. Nos. 3,089,824; 3,117,027; and 3,253,944. The coating is normally applied to the drug resin complex, but alternatively can be applied to the resin before complexing with the drug.

In the examples to follow the drug-resin complex particles are coated at a level of 16 percent by weight (as dry weight of the non-volatile solids of the coating, complex, and treating agent, if any) with a coating solution containing about 5% by weight ethylcellulose (50cps) (U.S.P. grade), about 2% by weight Durkex 500 refined vegetable oil, about 10% by weight acetone, and the balance methylene chloride. The coating solution is prepared by dissolving the Durkex and ethylcellulose in the acetone and methylene chloride. The coating of the complex particles is carried out in a fluid bed coating apparatus at a rate of 16–17 ml of coating solution per minute. The inlet air temperature is about 33° C. and the outlet air temperature is about 22°–25° C.

As shown in the control test below (Control), an untreated and uncoated resin-drug complex rapidly releases its drug (86.5% in 30 minutes) in a simulated gastric fluid (0.1 normal hydrochloric acid). Coated, but untreated, complex particles (Comparative Example) partially retard this release rate (30.9% release of drug in 30 minutes), but the release rate is further retarded (16.1–21.0% release in 30 minutes) when the complex particles are treated with polymeric agents prior to coating (Examples 1–3). While the polymer is normally applied to the complex, it may be applied to the resin particles prior to complexing, as in the case where the resin particles are coated prior to complexing with the drug. In the following examples the polymeric agent, dissolved in sufficient deionized water, is added to the PPA-resin complex and mixed (in a suitable planetary mixer) for about 10 minutes, then fluid bed dried to a moisture of less than 5%.

Variation in the amount of coating and/or the use of coated/uncoated complex mixtures can be employed to selectively modify the dissolution profile as desired. In addition to oral administration, the preparations of the subject invention are also suitable for topical, rectal or vaginal administration in dosages varying over a wide range, for example, from about 0.1 to about 1000 mg, depending on the nature of the drug and its intended usage. The compositions can take the form of tablets, powders, capsules, liquid suspensions or other conventional dosage forms.

The following dissolution test apparatus and procedures are used in the examples to simulate conditions encountered in the gastrointestinal tract: Five hundred ml of the dissolution medium (0.1N HCl) is placed in a round bottom flask immersed in a suitable water bath and the temperature allowed to rise to 37°±0.5° C. The flask is equipped with a paddle which is agitated at 100 rpm. The dissolution medium is pumped from the vessel through a cotton filter. Polyethylene tubing carries the filtered media via a peristaltic pump through a 1 cm flow cell of a Beckman model 35 recording spectrophotometer (equipped with a cell changer) and returns it to the vessel. The flow rate is adjusted to 16 ml/minute. In this way, each of the six vessels and a standard can be monitored at 15 minutes or other suitable intervals. The spectrophotometer is operated at 257 nm in a single beam mode to monitor six resin complex samples and one PPA hydrochloride standard. Each dissolution vessel contains resin complex sample equivalent to 90.6 mg of PPA base. The standard PPA solution contains 90.6 mg of PPA based in 500 ml of 0.1 N HCl. The drug released is then expressed as a percentage of the total drug present in the complex particles.

ILLUSTRATIVE EXAMPLES

CONTROL

Uncoated, Untreated Complex

PPA hydrochloride (96.84 kg) was dissolved in 850 liters of deionized water in a glass-lined mixing kettle. Amberlite IRP-70 resin (243.77 kg), washed hydrogen cycle, was then added to the stirring PPA hydrochloride solution. The mixing was continued for 2 hours. The PPA-resin slurry was then transferred to the holding tank and then to the centrifuge. The resin core was washed with deionized water for at least 10 minutes until free of chloride ions. The resin core was then dried to a moisture of less than 5% in a fluid bed dryer having a 70° C. inlet air temperature. The dried resin complex was found to contain 23.8% of phenylpropanolamine. Dissolution results are shown in Table I.

COMPARATIVE EXAMPLE

Coated, Untreated, Complex

Dissolution results on the PPA-resin complex particles, coated as descried hereinabove, are shown in Table I.

EXAMPLES 1 TO 3

Pretreated, Coated Complex

Three batches of coated PPA-resin complex particles were prepared, one of which was pretreated with about 0.8% Carbopol 934P (Example 1), one with about 0.07% xanthan gum (Example 2), and one with about 0.7% propylene glycol alginate (Example 3), all percents being by weight based on the weight of the resin and the polymer. The dissolution results are shown in Table I.

TABLE I

| | % PPA Released At: | | | |
|---|---|---|---|---|
| | 0.25 hr. | 0.5 hr | 1.0 hr. | 3.0 hr. |
| Control | 86.4 | 86.5 | 86.4 | 93.0 |
| Comparative Example | 21.0 | 30.9 | 41.7 | 58.1 |
| Example 1 | 15.9 | 21.0 | 29.4 | 41.2 |
| Example 2 | 14.2 | 20.9 | 25.3 | 43.7 |
| Example 3 | 11.4 | 16.1 | 20.9 | 37.7 |

Applying the foregoing discovery, controlled release dosage forms can be formulated for human or veterinary use to contain suitable mixtures of coated and uncoated complex particles such that a desired controlled release profile of the drug is obtained. The dosage forms can be solid (such as powders, capsules and tablets) or liquid (such as a suspension of complex particles in a palatable vehicle).

What is claimed is:

1. A process for enhancing the coatability of sulfonic acid cationic exchange resin particles which comprises contacting said particles with an aqueous solution containing from at least about 0.04% to about 1.1% by weight of a high molecular weight polymer, based on the combined weight of the polymer and the particles, said polymer being selected from the group consisting of carboxypolymethylene, xanthan gum, and propylene glycol alginate, and thereafter individually coating said particles with a water-permeable diffusion barrier.

2. The process of claim 1 wherein the polymer is carboxypolymethylene.

3. The process of claim 1 wherein the polymer is xanthan gum.

4. The process of claim 1 wherein the polymer is propylene glycol alginate.

* * * * *